United States Patent
Tsui

(10) Patent No.: US 8,361,402 B2
(45) Date of Patent: Jan. 29, 2013

(54) APPARATUS FOR AIR PURIFICATION AND DISINFECTION

(75) Inventor: Herman Yik Wai Tsui, Ferry Point (HK)

(73) Assignee: Alphatech International Limited, Hong Kong (HK)

( * ) Notice: Subject to any disclaimer, the term of this patent is extended or adjusted under 35 U.S.C. 154(b) by 1635 days.

(21) Appl. No.: 11/447,225

(22) Filed: Jun. 5, 2006

(65) Prior Publication Data

US 2007/0020159 A1    Jan. 25, 2007

Related U.S. Application Data

(60) Provisional application No. 60/700,740, filed on Jul. 20, 2005.

(51) Int. Cl.
*B01J 19/08* (2006.01)
(52) U.S. Cl. .............................. 422/186.07; 422/186.18
(58) Field of Classification Search ............. 422/186.07, 422/186.18
See application file for complete search history.

(56) References Cited

U.S. PATENT DOCUMENTS

| | | | | |
|---|---|---|---|---|
| 4,863,701 A | * | 9/1989 | McMurray | 422/186.08 |
| 4,954,320 A | * | 9/1990 | Birmingham et al. | 422/186.04 |
| 5,368,816 A | * | 11/1994 | Detzer | 422/28 |
| 5,552,125 A | * | 9/1996 | Chamblee et al. | 422/186.07 |
| 6,245,299 B1 | * | 6/2001 | Shiloh et al. | 422/121 |
| 6,905,659 B2 | * | 6/2005 | Usui et al. | 422/186.07 |
| 7,560,080 B2 | * | 7/2009 | Billing et al. | 422/186.07 |
| 7,713,495 B2 | * | 5/2010 | Wada et al. | 422/186.07 |
| 2005/0249646 A1 | | 11/2005 | Iwama et al. | |

FOREIGN PATENT DOCUMENTS

| | | |
|---|---|---|
| CN | 85104075 | 11/1986 |
| CN | 2621053 | 6/2004 |
| CN | 1611855 | 5/2005 |
| CN | 1614321 | 5/2005 |
| CN | 2713351 | 7/2005 |
| GB | 2177625 | 1/1987 |
| HK | 1056487 | 1/2004 |
| JP | 08-185999 | * 7/1996 |
| JP | 200135281 | 5/2000 |
| JP | 2001164926 | 6/2001 |
| JP | 2002221027 | 8/2002 |
| KR | 1020020000659 | 1/2002 |
| KR | 1020020083563 | 11/2002 |
| WO | WO 99/26726 | 6/1999 |
| WO | WO 99/47242 | 9/1999 |

* cited by examiner

*Primary Examiner* — Kishor Mayekar
(74) *Attorney, Agent, or Firm* — George G. Wang; Bei & Ocean

(57) ABSTRACT

An apparatus for air purification and disinfection is provided. The apparatus includes at least one elongated reactor having an elongated inner electrode and an elongated outer electrode. The outer electrode encompasses at least a portion of the inner electrode along a longitudinal axis of the reactor. The outer and inner electrodes are positioned in a substantially concentric relationship and define a reaction chamber therebetween. The apparatus also includes an inner electrode mounting member holding the inner electrode at an end of the inner electrode and an outer electrode mounting member holding the outer electrode at an end of the outer electrode. The apparatus further includes a power supply adapted to supplying electrical power to the inner and outer electrodes to generate plasma within the reaction chamber to purify and disinfect air flowing therethrough.

10 Claims, 13 Drawing Sheets

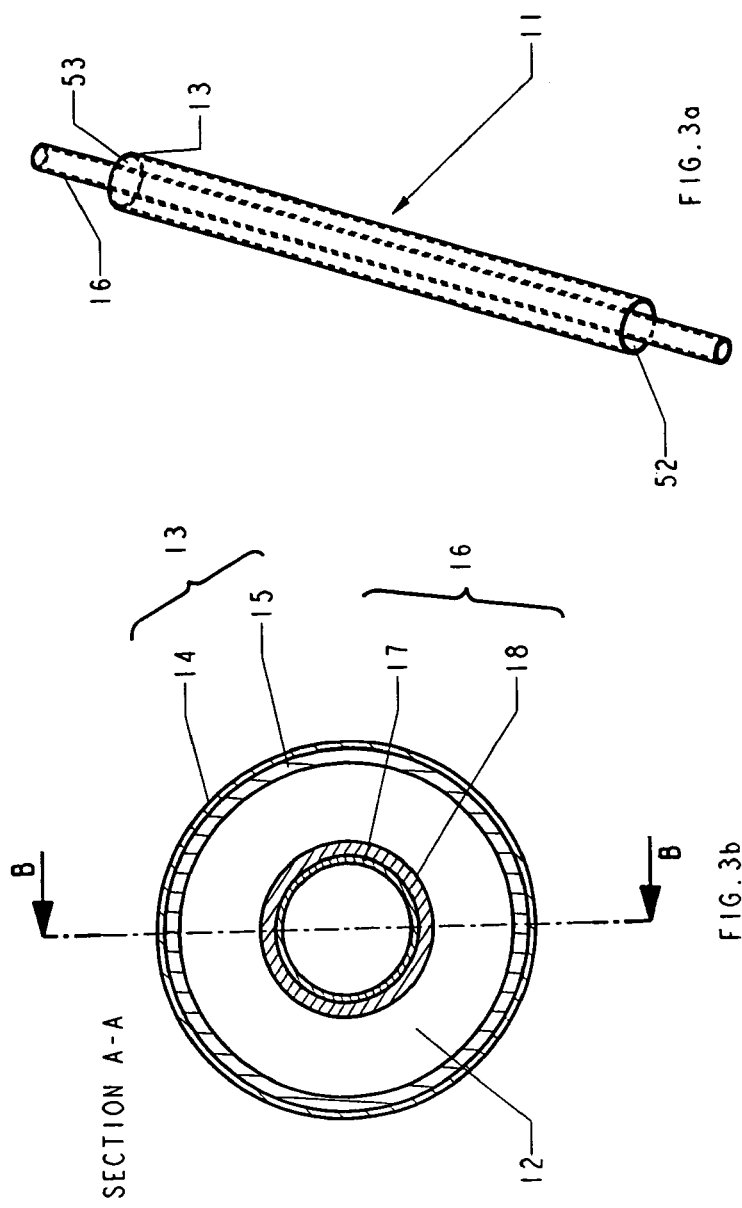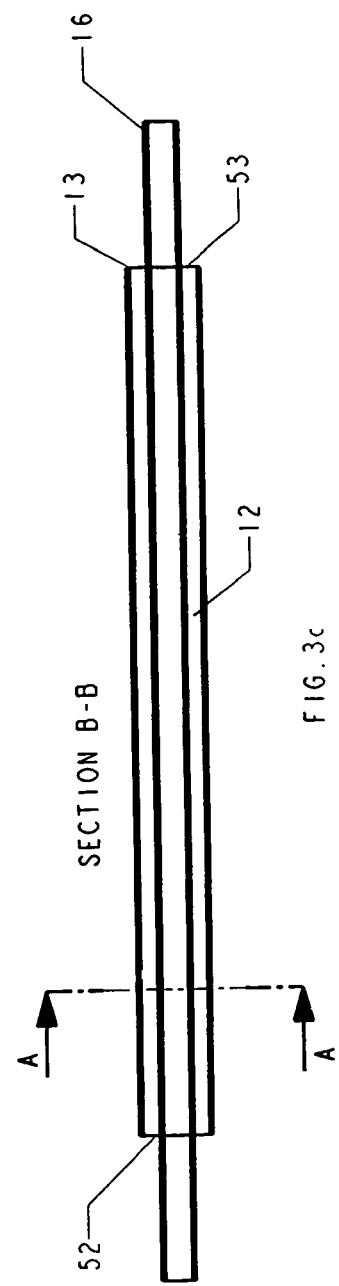

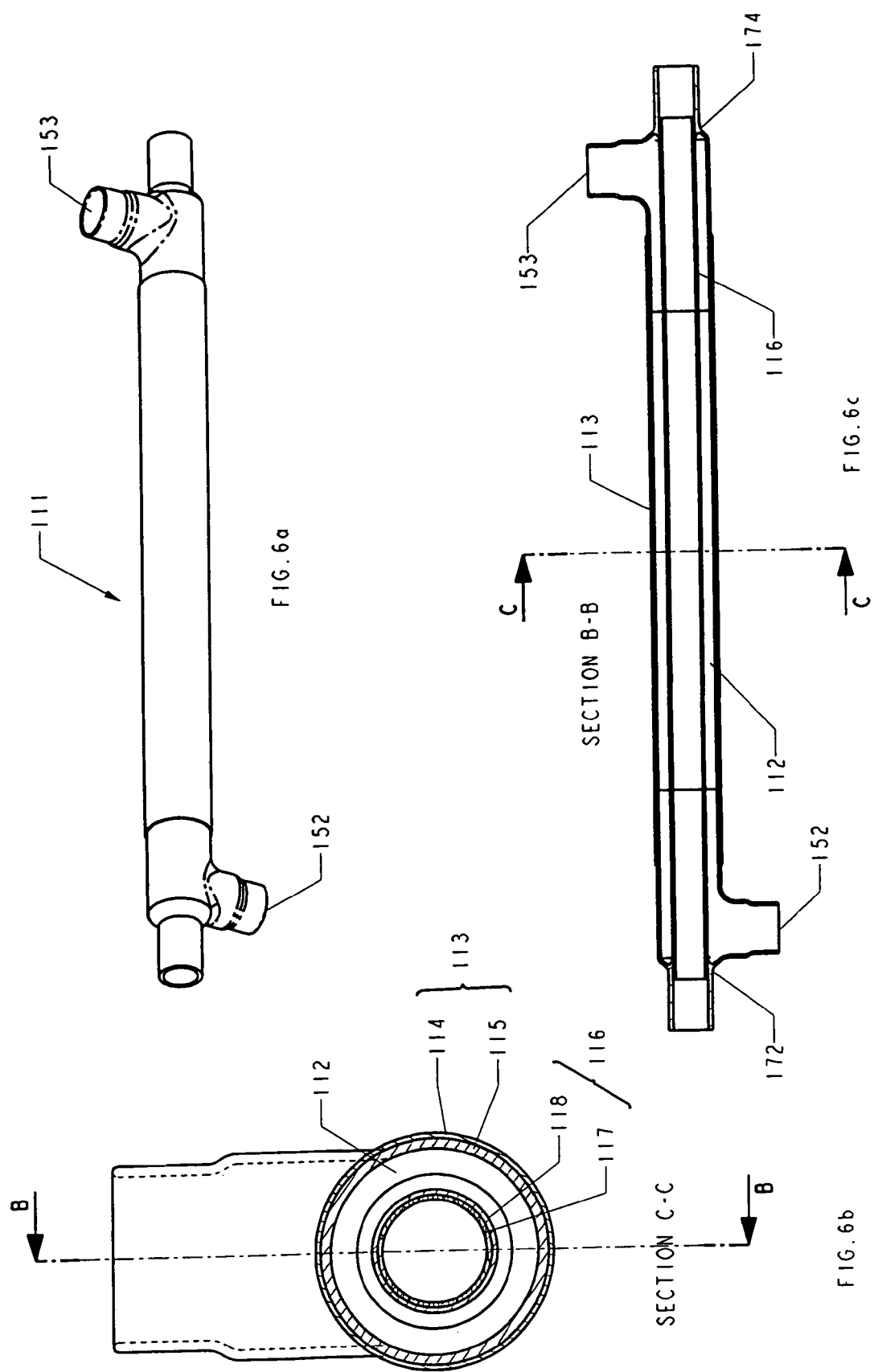

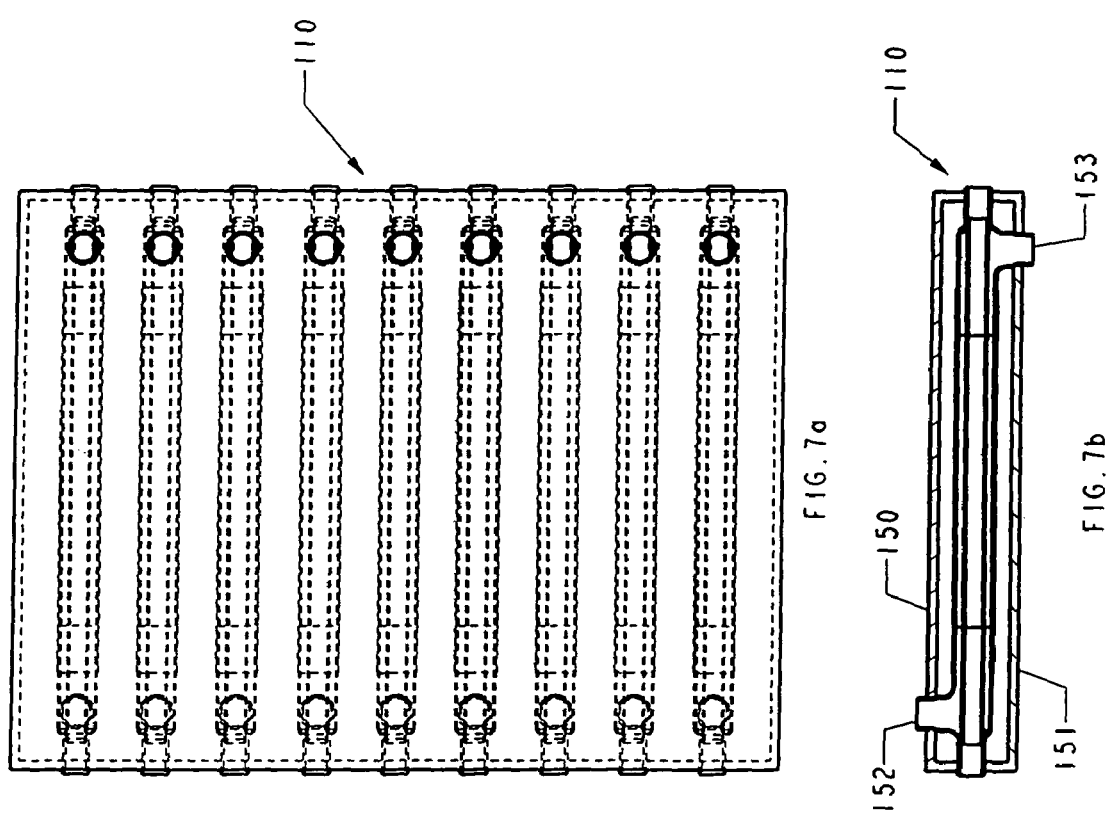

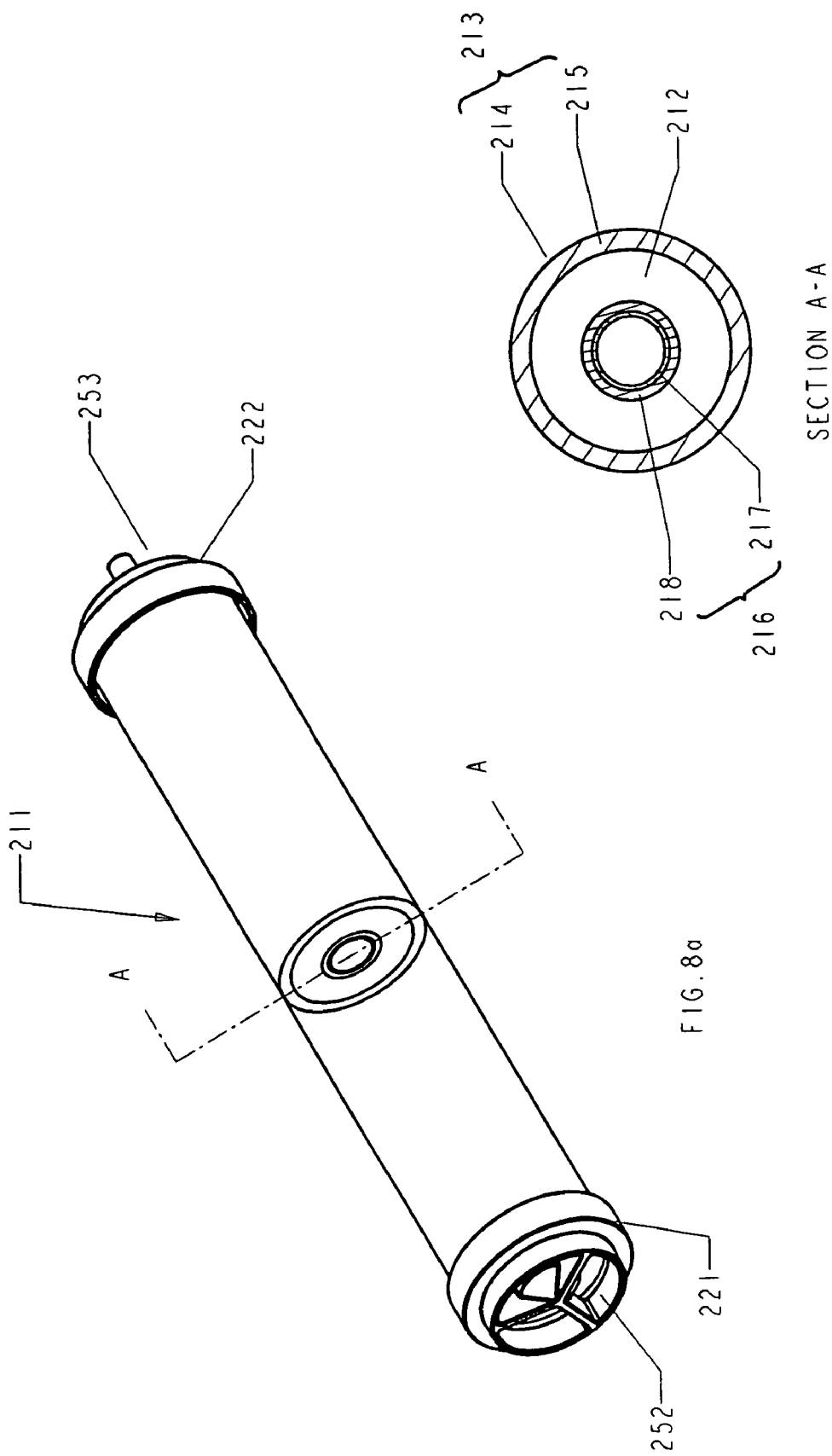

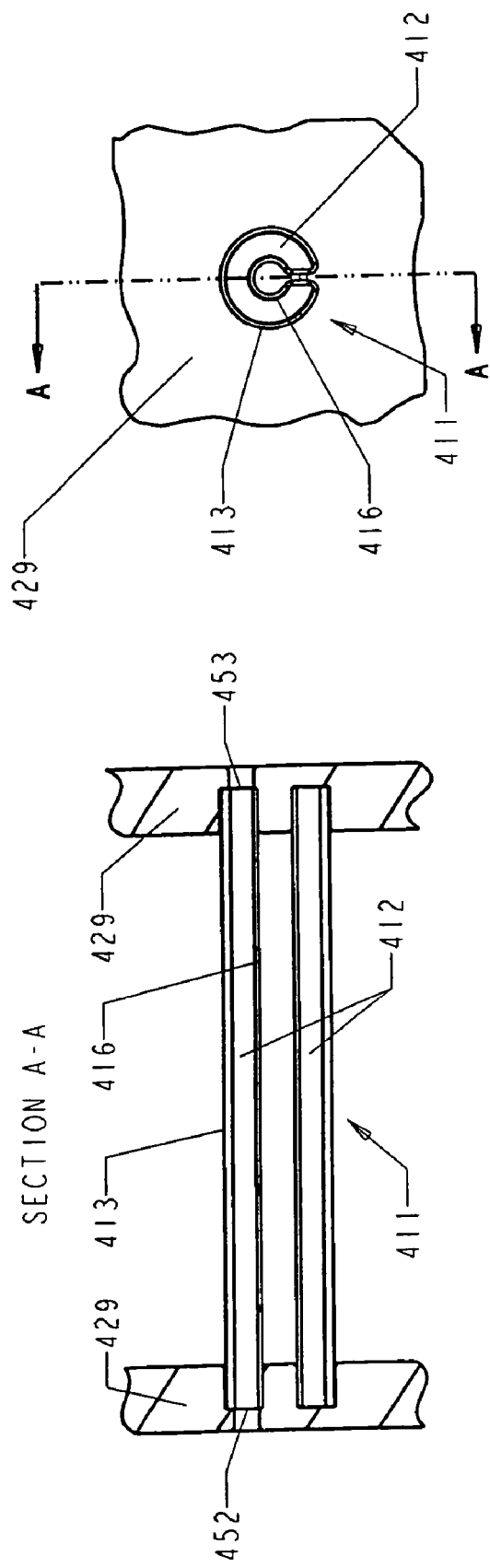

APPARATUS FOR AIR PURIFICATION AND DISINFECTION

CROSS-REFERENCE TO RELATED APPLICATION

This application claims the benefit of U.S. Provisional Patent Application No. 60/700,740, filed Jul. 20, 2005, which is hereby incorporated by reference in its entirety.

FIELD OF THE INVENTION

The present invention relates an apparatus for air purification and disinfection and more particularly to an apparatus for air purification and disinfection using plasma.

BACKGROUND

Available air purification apparatus in the marketplace can be broadly grouped into two principal types: i) removal of unwanted particles through trapping and filtration, and ii) destruction of unwanted particles to eliminated the associated harmful effects or render the harmful microbes (such as bacteria) unviable. Filtration based apparatus have air circulating through an air filtration device (filter) and particles above a certain size are trapped by the filter. Depending on the materials that make up the filter and its construction method, particles with a diameter of a few micrometers or larger can be removed from the circulating air. Some filtration devices incorporate additional apparatus (such as electrostatic precipitators) to introduce charges to the particles to enhance the trapping efficiency. Viruses are generally small enough to pass through these filters and microbes can also be carried by aerosol of sufficiently small size to pass through the filters. Filters trap them but do not destroy them. Some existing air purification systems incorporate ultraviolet (UV) light to destroy trapped microbes. Un-trapped microbes remain in the air.

Ion generators are also provided in the marketplace for the removal of airborne particles. They produce negative electrical charge and when the charge is applied to airborne particles, the airborne particles will fall out and cling to nearby surfaces. Therefore, these devices function only to separate and remove airborne harmful particles but not to destroy them.

There are also ozone ($O_3$) generators in the marketplace for the destruction of airborne microbes. Ozone is not an effective biocide for airborne microbes except at extremely high and unsafe levels, for example, more than 3,000 ppb. As a result, ozone generators cannot destroy airborne microbes or pathogenic microorganisms effectively to achieve any benefits to human health. If these devices accidentally generate excessive levels of ozone, it will be detrimental to health. In fact, there are many articles published giving warnings about use of excessive ozone for air disinfection.

UV has been successfully applied in some applications for disinfection. Research in UV disinfection of airborne microbes demonstrated that a residence time (i.e. the duration that an air stream needs to be radiated with UV) of the order minutes and hours is required to achieve noticeable level of disinfection. This level of efficiency is considered low in practical terms.

There are also articles reported that charged particles (ion clusters) can have disinfection effect. Similar to UV disinfection, the efficiency of this disinfection mechanism is also low and an exposure to the ion clusters of the order hours is typically required.

Plasma is an electrically neutral, ionized gas composed of freely moving ions, electrons, and neutral particles. Plasma is used today for a variety of commercial applications including for air purification and disinfection. Depending on the operation regime, plasma can consist of charged particles (electrons and ions), excited species, free radicals, ozone and UV photons, which are capable of decomposing chemical compounds and destroying microbes. Existing commercially available plasma air purifiers operate either indirectly by using ozone or UV photons generated by plasma contained in a separate device or by charging up the airborne particles in a similar fashion as ion generators operate.

Plasma can be created by electrical means in the form of gaseous discharges whereby a high voltage is applied to a set of electrodes, the anode and the cathode. When the applied voltage is sufficiently high and becomes greater than the breakdown voltage, arcs begin to develop across the electrodes. The threshold for electrical breakdown or arc formation follows the well-known Paschen law, which relates the breakdown voltage to the gap size between the electrodes and the gas pressure.

Breakdown occurs when the applied voltage, or more precisely the local electric field, is sufficiently large for electrons to acquire enough energy to compensate the energy losses due to collisions, excitation and other energy loss processes. The breakdown process begins with presence of some free or residual electrons accelerating towards the anode under the influence of the externally applied electric field. As they accelerate towards the anode, the streaming electrons collide with the gas atoms causing ionization directly by impact or indirectly through photo-ionization. An electron cloud begins to build up and propagates towards the anode together with an ionization or breakdown front ahead of the electron cloud, leaving an ion trail behind, resulting in a plasma channel with an electric dipole opposing the applied electric field. The formation of such streamer, if unrestrained, leads to a rapid increase in charge density, fast growth of an avalanche, and the transformation of the streamer into an arc.

By introducing suitable current limiting or quenching mechanism(s) to prevent the development of major arcs, a quasi-steady state can be established with micro-arcs or filaments (of dimension of the order of $10^{-4}$ m) filling up the gap between the electrodes. Traditionally this is achieved by placing dielectric barrier or insulator covering one or both electrodes. Discharge having an insulating or dielectric layer incorporated on one or both of the electrodes is known as dielectric-barrier discharge. The non-conducting property of the dielectric or insulating layer allows charge accumulation on the surface, which produces an opposite electric field to the applied electric field. In addition, the space charge built up next to the dielectric or insulating layer adds to the electron repelling electric field. The opposing electric field cancels the applied electric field and prevents a filament from developing into a major arc and causes a discharge filament to extinguish. Therefore, the low charge mobility on the dielectric leads to self-arresting of the filaments and also limits their lateral extension, thereby allowing multiple filaments to form in close proximity to one another. Furthermore, when coalescence of multiple ionization fronts occurs, the filamentary discharge transforms to a diffuse glow discharge that has spatially more uniform properties. Current quenching can also be achieved by carefully controlling the applied voltage to prevent transition into an arc. It can be created by the use of needle-like electrodes to create a space charge region around the smaller or sharper electrode. It can also be achieved by including non-conducting packing materials in a bed residing between the electrodes.

In a dielectric-barrier discharge operating in the near-atmospheric pressure range, electron energy is typically in the range of 1 to 10 eV and ion energy is close to the ambient gas temperature. Because of the energy disparity between the electron and ion species, these discharges are classified as non-thermal plasma. Typically, the density of the charge particles is much less than the neutral ambient gas and the plasma behavior is dominated by collisional effects. The energy of the electrons can be utilized for exciting atoms and molecules, thereby initiating chemical reactions and/or emission of radiations. The energetic electrons are able to induce the breakdown of some chemical bonds of the molecules, collide with the background molecules resulting in the breakdown of molecular chain, ionization and excitation, and generation of free atoms and radicals such as O, OH or $HO_2$. The radicals can attack hazardous organic molecules and are useful in decomposing pollutants in air. The disassociation of $O_2$ provides the required O to combine with $O_2$ to form ozone. The low energy electrons can attach to neutral atoms or molecules to form negative ions, which can enhance reactions in decomposing pollutants and destruction of microbe. Through collision, electrons can destroy organic compounds including bacteria and virus directly. Emissions, particularly in the UV spectral region, through recombination and relaxation, can initiate photo-physical and photo-chemical process by breaking molecular bonds and hence destroying microbe resulting in disinfection effect.

The harmful contaminants can be broadly grouped into chemical contaminant, volatile organic compounds, bacteria, fungi and viruses; each group is characterized by the amount and complexity of the constituent molecules or radicals. Plasma properties have to be optimized in order to destroy and/or to prevent the growth of these harmful contaminants. One major requirement is to ensure that these harmful contaminants have an adequate residence time within the reactor device while supporting a sufficiently high flow rate for practical applications.

While plasma can be utilized to reduce the harmful particles, the generation of plasma also creates by-product gas which can be hazardous. Typical examples of bi-product gas are ozone and nitrogen dioxide ($NO_2$).

Therefore it would be desirable to provide an apparatus to generate plasma for indoor air purification and disinfection which adequate residence time and effective plasma power deposition to achieve efficient destruction of pollutants while minimizing the generation unwanted bi-product gases.

SUMMARY

An apparatus for air purification and disinfection is provided. In one aspect, the apparatus includes at least one elongated reactor having an elongated inner electrode and an elongated outer electrode. The outer electrode encompasses at least a portion of the inner electrode along a longitudinal axis of the reactor. The outer and inner electrodes are positioned in a substantially concentric relationship and define a reaction chamber therebetween. The apparatus also includes an inner electrode mounting member holding the inner electrode at an end of the inner electrode and an outer electrode mounting member holding the outer electrode at an end of the outer electrode. The apparatus further includes a power supply adapted to supplying electrical power to the inner and outer electrodes to generate plasma within the reaction chamber to purify and disinfect air flowing therethrough.

The reaction chamber of the reactor may include an air inlet and an air outlet positioned at opposite ends thereof. The outer electrode mounting member may include an opening corresponding to the air inlet or the air outlet of the reaction chamber of the reactor.

In one embodiment, the inner electrode is longer than the outer electrode. In another embodiment, the inner electrode mounting member includes a protruded portion holding the inner electrode.

In one embodiment, the apparatus includes a plurality of elongated reactors positioned in generally parallel with each other.

In one embodiment, the outer electrode includes an insulator layer and an electrode conductor covered at the outer surface of the insulator layer, while the inner electrode includes an insulator layer and an electrode conductor covered at the inner surface of the insulator layer. In another embodiment, the outer electrode includes an insulator layer and an electrode conductor embedded in the insulator layer, while the inner electrode includes an insulator layer and an electrode conductor embedded in the insulator layer.

In one embodiment, the power supply includes a control unit adapted to control the electrical power supplied to the inner and outer electrodes of the reactor. The waveform period and the on/off cycle of the electrical power are set to be shorter than the time that the air stays inside the reaction chamber.

In another aspect, the apparatus for air purification and disinfection includes at least one elongated reactor having an elongated inner electrode and an elongated outer electrode. The outer electrode encompasses the inner electrode along a longitudinal axis of the reactor. The outer and inner electrodes are positioned in a substantially concentric relationship and define a reaction chamber therebetween. The insulator layer of the inner electrode and the insulator layer of the outer electrode are integrally joined together. The apparatus further includes a power supply adapted to supplying electrical power to the inner and outer electrodes to generate plasma within the reaction chamber to purify and disinfect air flowing therethrough.

The reaction chamber of the reactor may include an air inlet and an air outlet positioned at opposite ends thereof.

In one embodiment, the insulator layer of the inner electrode and the insulator layer of the outer electrode are integrally joined at a first end of the reactor. The insulator layer of the inner electrode and the insulator layer of the outer electrode may be integrally joined at a second end of the reactor. In another embodiment, the insulator layer of the inner electrode and the insulator layer of the outer electrode are integrally built along the longitudinal axis of the reactor.

In one embodiment, the apparatus includes a plurality of elongated reactors positioned in generally parallel with each other.

In one embodiment, the outer electrode includes an insulator layer and an electrode conductor covered at the outer surface of the insulator layer, while the inner electrode includes an insulator layer and an electrode conductor covered at the inner surface of the insulator layer. In another embodiment, the outer electrode includes an insulator layer and an electrode conductor embedded in the insulator layer, while the inner electrode includes an insulator layer and an electrode conductor embedded in the insulator layer.

In one embodiment, the power supply includes a control unit adapted to control the electrical power supplied to the inner and outer electrodes of the reactor. The waveform period and the on/off cycle of the electrical power are set to be shorter than the time that the air stays inside the reaction chamber.

In another aspect, the apparatus for air purification and disinfection includes at least one elongated reactor having an elongated inner electrode, an elongated outer electrode and a first end cap. The outer electrode encompasses the inner electrode along longitudinal axis of the reactor. The outer and inner electrodes are positioned in a substantially concentric relationship and define a reaction chamber therebetween. The first end cap couples the inner electrode and the outer electrode at a first end of the reactor. The apparatus further includes a power supply adapted to supplying electrical power to the inner and outer electrodes to generate plasma within the reaction chamber to purify and disinfect air flowing therethrough.

The apparatus may includes a second end cap coupling the inner electrode and the outer electrode at a second end of the reactor.

The reaction chamber of the reactor may include an air inlet and an air outlet positioned at opposite ends thereof.

In one embodiment, the apparatus includes a plurality of elongated reactors positioned in generally parallel with each other.

In one embodiment, the outer electrode includes an insulator layer and an electrode conductor covered at the outer surface of the insulator layer, while the inner electrode includes an insulator layer and an electrode conductor covered at the inner surface of the insulator layer. In another embodiment, the outer electrode includes an insulator layer and an electrode conductor embedded in the insulator layer, while the inner electrode includes an insulator layer and an electrode conductor embedded in the insulator layer.

In one embodiment, the power supply includes a control unit adapted to control the electrical power supplied to the inner and outer electrodes of the reactor. The waveform period and the on/off cycle of the electrical power are set to be shorter than the time that the air stays inside the reaction chamber.

BRIEF DESCRIPTION OF THE DRAWINGS

FIG. 1b is an enlarged view of the circled portion of the reactor assembly shown in FIG. 1a.

FIG. 3a is a perspective view of one of the reactors of the reactor assembly of FIG. 1a.

FIG. 3b is a cross-sectional front view of the reactor of FIG. 3a, showing the reaction chamber between the inner and outer electrodes.

FIG. 3c is a cross-sectional side view of the reactor of FIG. 3a, showing two electrodes and the reaction chambers between the two electrodes.

FIG. 4 is a schematic diagram of an electrical circuit of an air purification and disinfection apparatus which utilize at least one reactor of FIG. 3a.

FIG. 5a is a perspective view of an air purification and disinfection apparatus incorporating the reactor assembly of FIG. 1a.

FIG. 5b is an exploded view of the air purification and disinfection apparatus shown in FIG. 5a.

FIG. 6a is a perspective view of another embodiment of a reactor.

FIG. 6b is a cross-sectional front view of the reactor of FIG. 6a.

FIG. 6c is a cross-sectional side view of the reactor of FIG. 6a.

FIG. 7a is a top view of a corresponding reactor assembly for the reactors shown in FIG. 6a.

FIG. 7b is a cross-sectional side view of the reactor assembly of FIG. 7a.

FIG. 8a is a perspective view of another embodiment of a reactor.

FIG. 8b is a cross-sectional front view of the reactor shown in FIG. 8a.

FIG. 8c is an exploded view of the reactor shown in FIG. 8a.

FIG. 9 is a perspective view of a corresponding reactor assembly for the reactors shown in FIG. 8a.

FIG. 11a is a cross-sectional side view of another embodiment of a reactor assembly showing a reactor and electrode mounting members.

FIG. 11b is a cross-sectional front view of the reactor assembly of FIG. 11a.

DETAILED DESCRIPTION

Reference will now be made in detail to certain embodiments of the invention, examples of which are also provided in the following description. Exemplary embodiments of the invention are described in detail, although it will be apparent to those skilled in the relevant art that some features that are not particularly important to an understanding of the invention may not be shown for the sake of clarity.

Furthermore, it should be understood that the invention is not limited to the embodiments described below and that various changes and modifications thereof may be effected by one skilled in the art without departing from the spirit or scope of the invention. For example, elements and/or features of different illustrative embodiments may be combined with each other and/or substituted for each other within the scope of this disclosure and appended claims.

In addition, improvements and modifications which may become apparent to persons of ordinary skill in the art after reading this disclosure, the drawings, and the appended claims are deemed within the spirit and scope of the present invention.

Figure 1A:
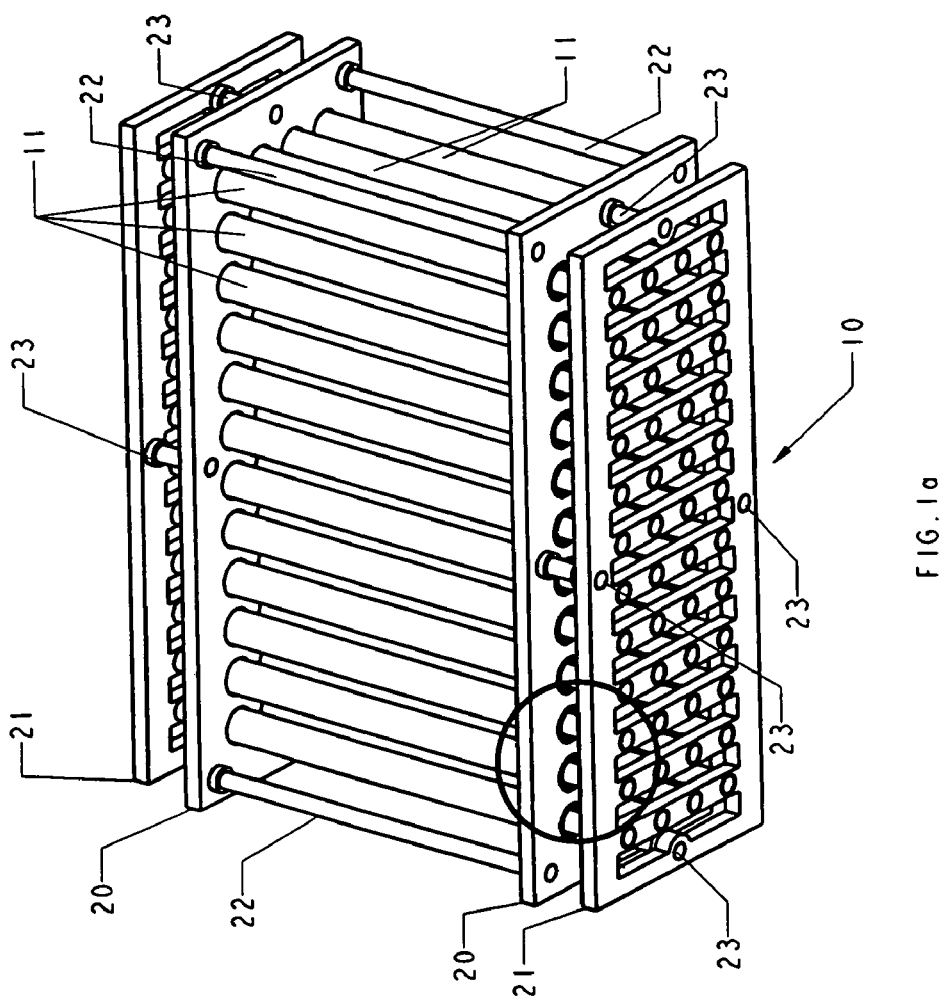
FIG. 1a is a perspective view of an embodiment of a reactor assembly of an air purification and disinfection apparatus.
Figure 1B:
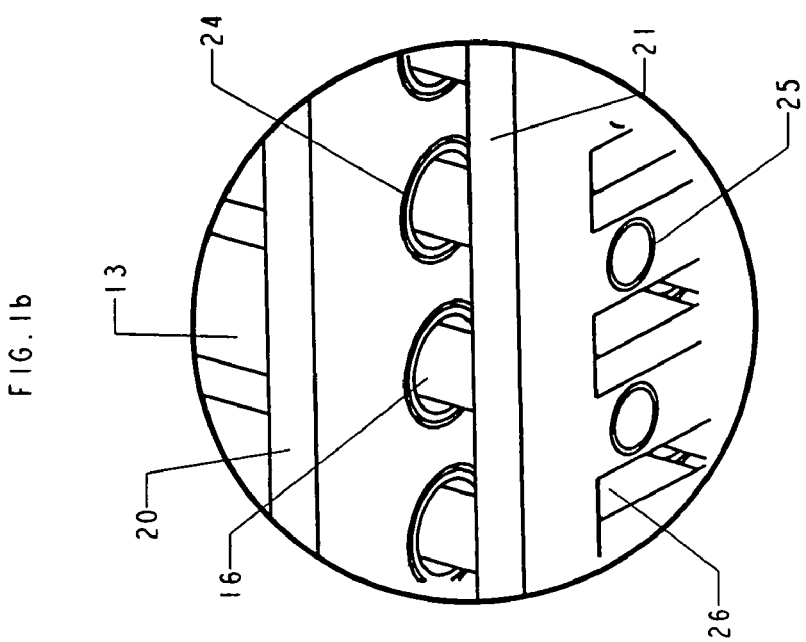

Referring now to the drawings, FIG. 1a shows a reactor assembly 10 of an air purification and disinfection apparatus. The reactor assembly 10 includes a plurality of reactors 11 which are elongated and can be arranged in generally parallel with each other. The reactors can be fixed in the reactor assembly 10 by mounting members 20, 21 and supporting members 22, 23. As shown in FIG. 1b, each of the reactors 11 includes an elongated outer electrode 13 and an elongated inner electrode 16. Each outer electrode 13 may be held in place by at least one outer electrode mounting member 20, and each inner electrode 16 may be held in place by at least one inner electrode mounting member 21.

Figure 2:
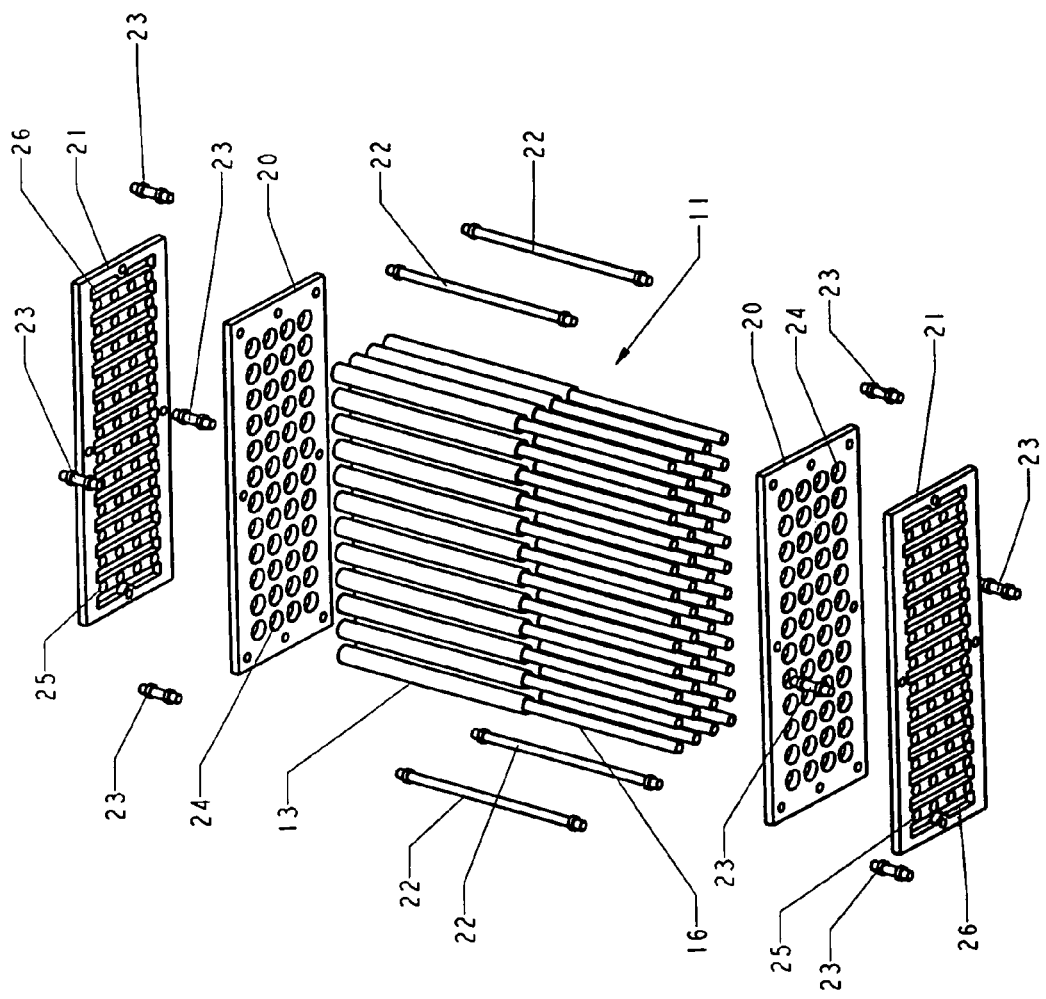
FIG. 2 is an exploded view of the reactor assembly of FIG. 1a, showing the arrangement of the reactors.

FIG. 2 illustrates in more details the construction of the reactor assembly 10 shown in FIG. 1a. The outer electrodes 13 may be held in place on both ends by the outer electrode mounting members 20 having openings 24. The inner electrodes 16 may be held in place on both ends by the inner electrode mounting members 21 having openings 25. The two outer electrode mounting members 20 may be held together by a plurality of supporting members 22. The inner electrode mounting members 21 may be fixed onto the outer electrode mounting members 20 by a plurality of supporting members 23. The generally parallel configuration of the reactors 11 can achieve a desired level of residence time for effective destruction of the contaminants. The residence time is the duration of the air flowing through the space between the outer electrode 13 and inner electrode 16.

FIGS. 3a-3d show an embodiment of the reactor 11 of the reactor assembly of FIG. 1a. In the illustrated embodiment, the reactor 11 is in cylindrical shape. The reactor 11 includes the outer electrode 13 and the inner electrode 16. The outer electrode 13 encompasses a portion of the inner electrode along a longitudinal axis of the reactor 11. The outer electrode 13 and the inner electrode 16 can be in a substantially concentric relationship. The outer electrode 13 and the inner electrode 16 define a reaction chamber 12 therebetween, which isolates the outer electrode 13 and the inner electrode 16. In the reaction chamber 12, electrical discharges are excited to generate plasma. The reactor 11 includes an air inlet 52 and an air outlet 53. The air inlet 52 and the air outlet 53 face to directions opposite with each other.

In the illustrated embodiment, the inner electrode 16 is longer than the outer electrode 13. Two end of the inner electrode 16 are positioned without being encompassed by the outer electrode 13. Therefore, the inner electrode 16 and the outer electrode 13 can be held in place by the outer electrode mounting members 20 and the inner electrode mounting members 21, respectively, as shown in FIG. 2. The air inlet 52 and the air outlet 53 correspond to the openings 24 on the outer electrode mounting members 20, such that the air to be purified can flow through the openings 24.

The outer electrode 13 includes an insulator layer 15 and an electrode conductor 14 covered at the outer surface of the insulator layer 15. The conductor 14 can be held in place by a number of different ways, for example, mechanical force, adhesive etc. Alternatively, the conductor 14 can be embedded inside the insulator 15. The inner electrode 16 includes an insulator layer 18 and an electrode conductor 17 covered at the inner surface of the insulator layer 18. Similar in construction to the outer electrode, the conductor 17 can be held in place by a number of different ways, for example, mechanical force, adhesive etc, or it can be embedded inside the insulator 18. In the illustrated embodiment, the inner and outer insulators 18 and 15 are made of insulating materials, such as glass, and can be tubular in shape. The electrode conductors 14 and 17 may be made of conducting sheets, mesh or deposits.

Electrical discharges are created in the reaction chamber 12 to generate plasma for air disinfection and purification. The energetic electrons excite atoms and molecules, thereby initiating chemical reactions and emission of radiations. The resultant radiations may induce breakdown of some chemical bonds of the molecules. The energetic electrons collide with the background molecules resulting in the breakdown of molecular chain, ionization and excitation, and generation of free atoms and radicals such as O, OH or $HO_2$. These products and reactions can dissociate hazardous organic molecules and decompose pollutants in air. By circulating air through the plasma-filled reaction chamber 12, the pollutant particles and microbes in the air would be destructed.

The number of reactors 11 within the reactor assembly 10 can be adjusted to match the total airflow requirement of the air purification and disinfection apparatus. Such scalable and modular design allows flexibility in construction so that the reactor assemble 10 can be readily incorporated as part of a central ventilation system or an air conditioner or as a stand-alone air purifier on its own.

Although the outer electrodes 13 and the inner electrodes 16 are held by the electrode mounting members 20 and 21, respectively, as shown in FIG. 2, it is to be understood that outer electrodes 13 and the inner electrodes 16 can be held by other mounting structures.

Figure 4:
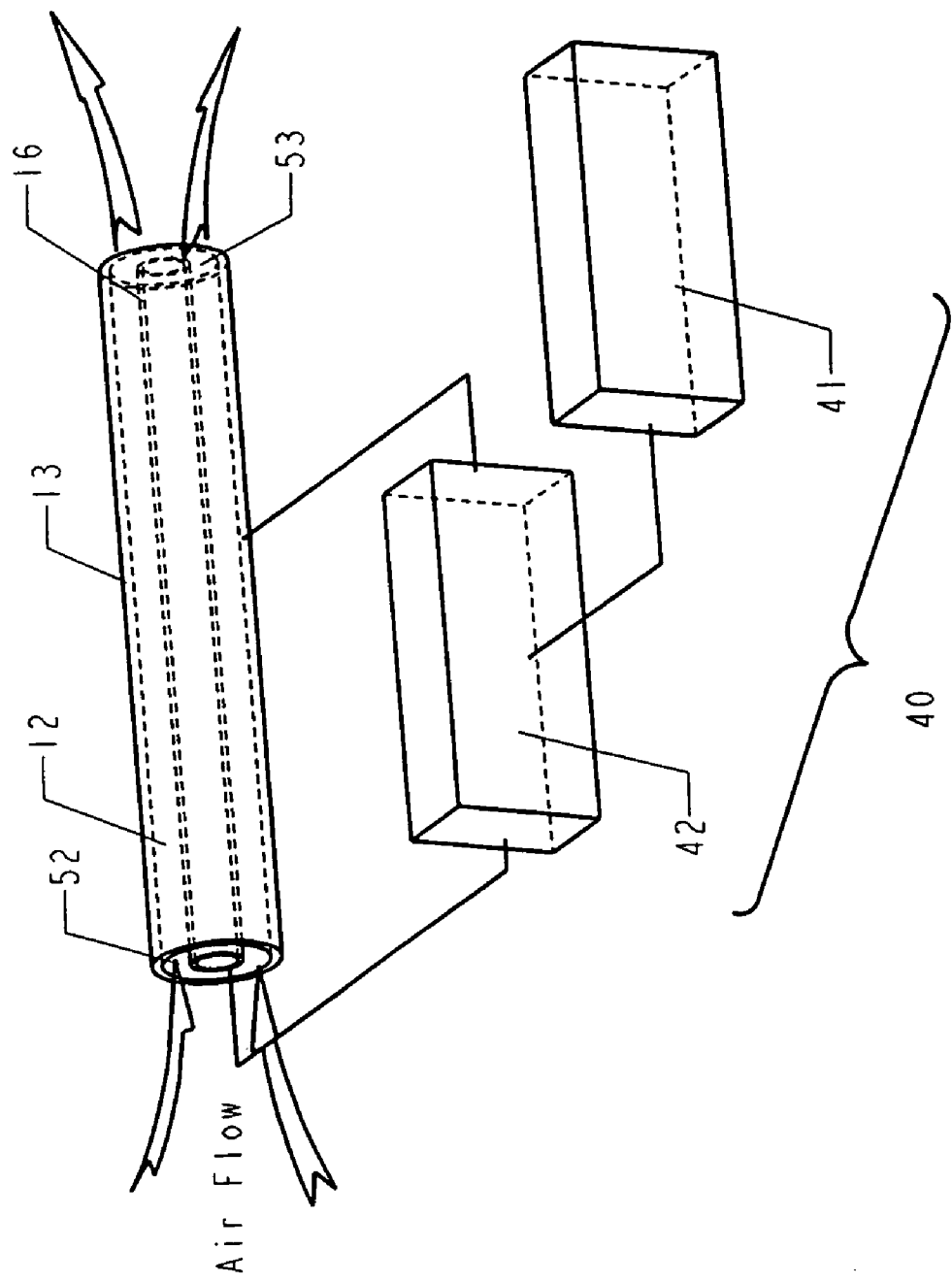

As illustrated in the schematic diagram FIG. 4, the electrodes 13 and 16 can be connected to a high-voltage alternating current (AC) power supply 40. In the illustrated embodiment, the power supply 40 includes an electronic control unit 41 and a high-voltage generator 42. The power supply 40 can provide sufficient voltage to cause breakdown and to generate plasma in the reaction chamber 12. With an annular space of the reaction chamber 12 typically in the range of 2 mm to 20 mm, the applied voltage may be in the range of 10-50 kV. The waveform period (typically in the range of $10^{-1}$ to $10^2$ ms) and shape can be selected to match the size of the annular space of the reaction chamber 12 and the electrodes as well as the residence time of the air passing through the reaction chamber 12. For example, with a reaction chamber of 12 mm wide and an inner radius of the outer electrode of 18 mm, the cross-sectional area of the reaction chamber 12 is about 9 $cm^2$. For each reactor 11 to support an air flow of 1000 l/min, the residence time is about 8 ms and the waveform period can be 8 ms or less.

The electronic control unit 41 can generate the required waveform shape and period to drive the high-voltage generator 42 which may produce the necessary high-voltage to generate plasma and may maintain the reactors to operate at specific decomposition and destruction effort. The waveform period and the on/off cycle of the electrical power are adjustable and can be set to be shorter than the time the air stream stays inside the reaction chamber. The plasma strength can be controlled by adjusting the applied high voltage and the ratio of the on-cycles to the off-cycles within the residence time.

Figure 5A:
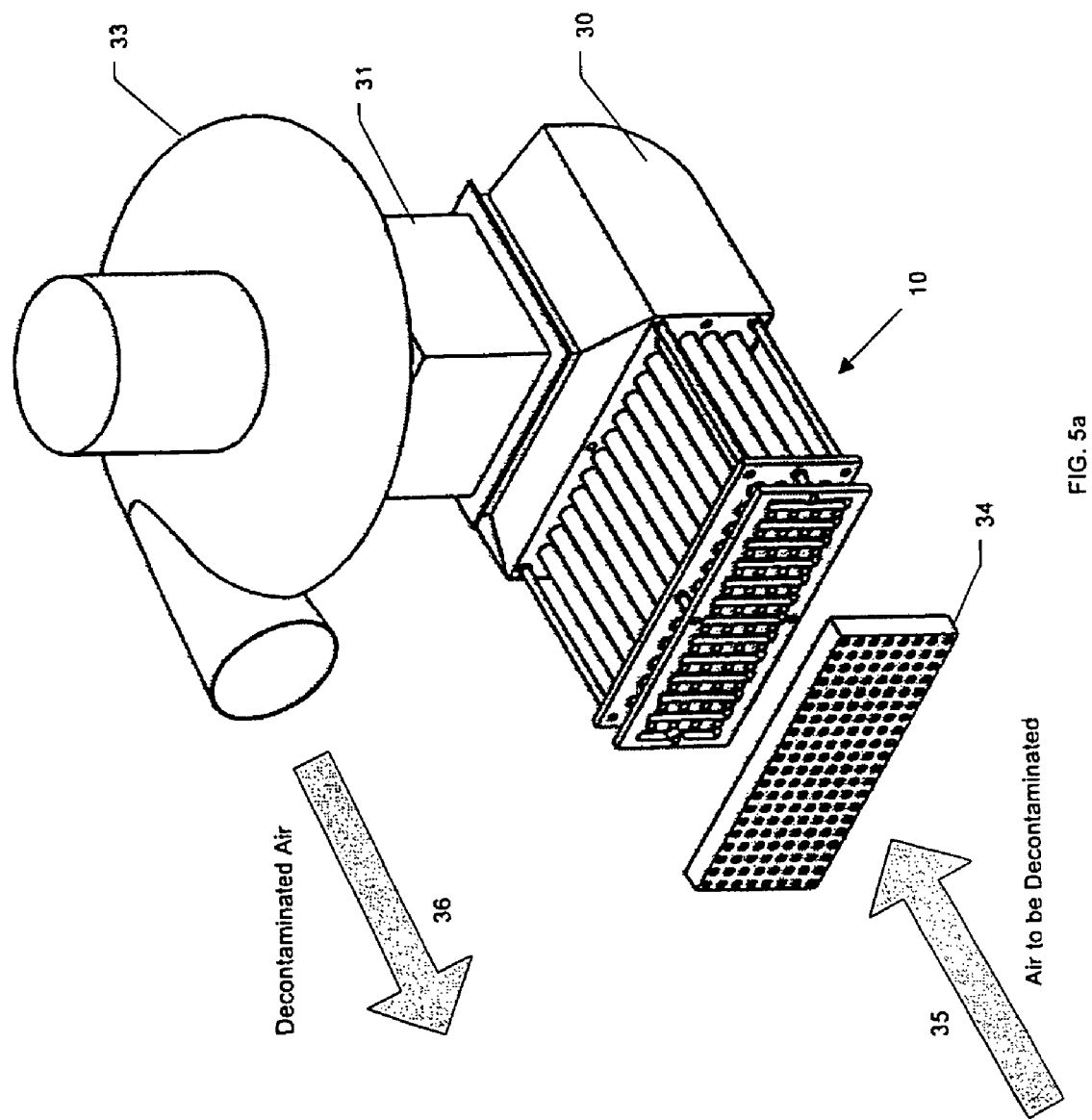
Figure 5B:
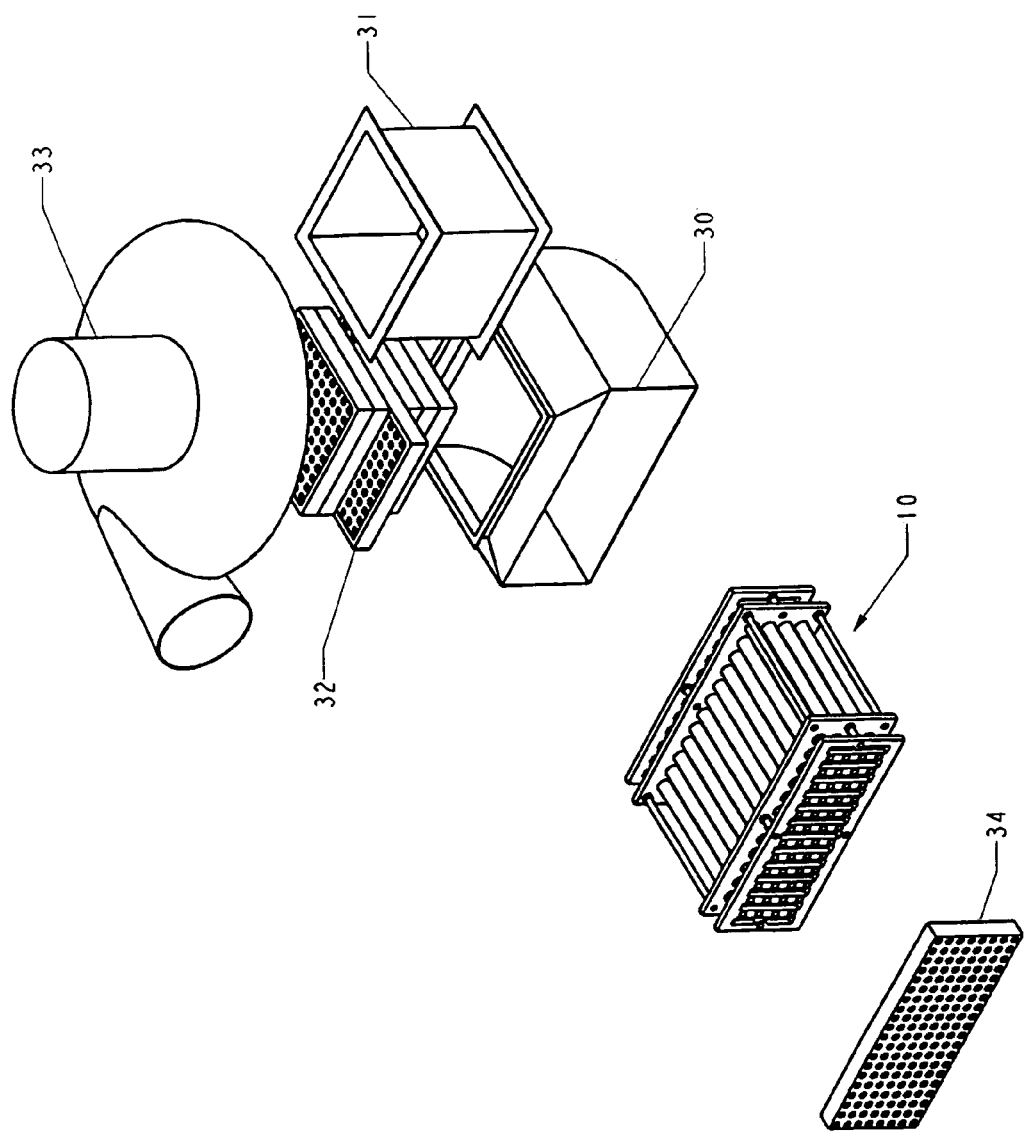

FIG. 5a shows an air purification and disinfection apparatus incorporating the reactor assembly 10. FIG. 5b provides an exploded view of the air purification and disinfection apparatus of FIG. 5a. In the illustrated embodiment, the air purification and disinfection apparatus includes a blower 33 and the reactor assembly 10 fitted inside a reactor-housing 30. Optionally, the air purification and disinfection apparatus includes filters 32 fitted inside a filter-housing 31 and a coarse filter 34.

During operation, air to be decontaminated 35 is drawn through the coarse filter 34 to remove large particles and dust before it is drawn into the reaction chambers 12 where disinfection and purification take place. The treated air is then drawn through a set of filters 32 and finally expelled by the blower 33 as decontaminated air 36.

FIGS. 6a-6c show another embodiment of a reactor 111. In this embodiment, the reactor 111 is elongated and in cylindrical shape. The reactor 111 includes an elongated outer electrode 113 and an elongated inner electrode 116. The outer electrode 113 encompasses the inner electrode along a longitudinal axis of the reactor 111. The outer electrode 113 and the inner electrode 116 can be in a substantially concentric relationship. The outer electrode 113 and the inner electrode 116 define a reaction chamber 112 therebetween, which isolates the outer electrode 113 and the inner electrode 116. In the reaction chamber 112, electrical discharges are excited to generate plasma.

The inner electrode 116 includes an inner insulator 118 and an inner electrode conductor 117 covered at the inner surface of the inner insulator 118. The outer electrode 113 includes an outer insulator 115 and an outer electrode conductor 114 covered at the outer surface of the outer insulator 115. The inner and outer insulators 118 and 115 are made of insulating materials, such as glass, and can be tubular in shape. The electrode conductors 114 and 117 may be made of conducting sheets, mesh or deposits.

In the illustrated embodiment, the reactor 111 is an integral unit where the inner and outer insulators 118 and 115 are joined together at the two ends 172 and 174 of the reactor 111. The conductors 114 and 117 can be held in place to their respective insulators 115 and 118 by a number of different ways, for example, mechanical force, adhesive etc., or alternatively, they can be embedded inside their corresponding insulators 115 and 118. A plurality of these reactors 111 can be held on mounting members in a generally parallel configuration to achieve the desired level of residence time for effective destruction of contaminants.

In use, air enters the reaction chamber 112 through an air inlet 152 provided on one side of the outer tube 115 facing to a first direction, and exits via an air outlet 153 provided along another side of the outer tube 115 facing a second direction. In the illustrated embodiment, the air inlet 152 faces to the first direction generally perpendicular to the longitudinal axis of the reactor 111, and the air outlet 153 faces to the second direction also generally perpendicular to the longitudinal axis of the reactor 111. By circulating air through the plasma-filled reaction chamber 112 inside the integral insulator, the pollutant particles and microbes in the air can be destructed. The air inlet 152 and air outlet 153 can be oriented in different directions in such a way to suit the required airflow path.

FIGS. 7a and 7b show a corresponding reactor assembly 110 for the embodiment of the reactor 111. The upper mounting member 150 and the lower mounting member 151 together hold the reactors 111 in place and form the reactor assembly 110.

Figure 8C:
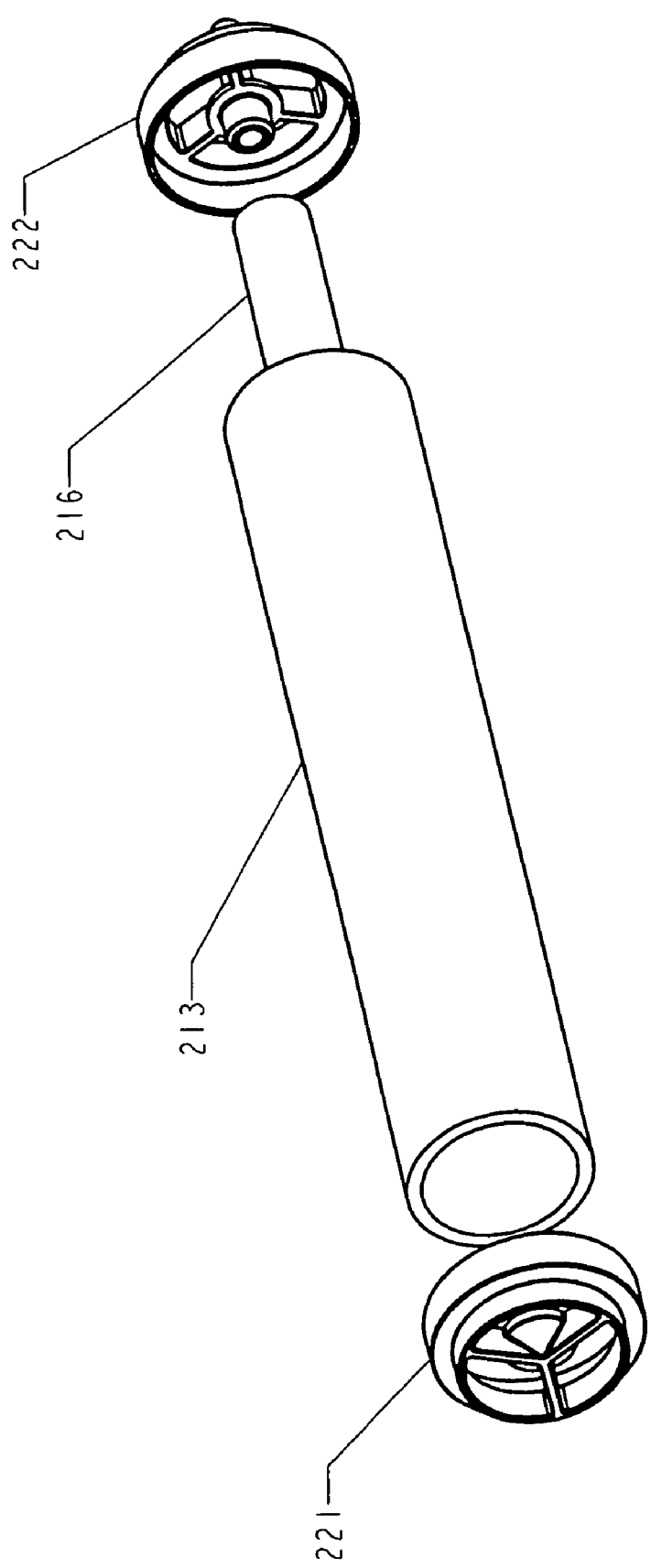

FIGS. 8a-8c show another embodiment of a reactor 211. In this embodiment, the reactor 211 is elongated and in cylindrical shape. The reactor 211 includes an elongated outer electrode 213 and an elongated inner electrode 216. The outer electrode 213 encompasses the inner electrode along the longitudinal axis of the reactor 211. The outer electrode 213 and the inner electrode 216 can be in a substantially concentric relationship. The outer electrode 213 and the inner electrode 216 define a reaction chamber 212 therebetween, which isolates the outer electrode 213 and the inner electrode 216. In the reaction chamber 212, electrical discharges are excited to generate plasma. End caps 221 and 222 hold the outer electrode 216 and the inner electrode 213 at two ends of the reactor 211. The length of the outer electrode 216 is substantially equal to the length of the inner electrode 213.

The inner electrode 216 includes an inner insulator 218 and an inner electrode conductor 217 covered at the inner surface of the inner insulator 218. The outer electrode includes an outer insulator 215 and an outer electrode conductor 214 covered at the outer surface of the outer insulator 215. The conductors 214 and 217 can be held in place to their respective insulators 215, 218 by a number of different ways, for example, mechanical force, adhesive etc., or alternatively, they can be embedded inside their corresponding insulators 215, 218.

Figure 9:
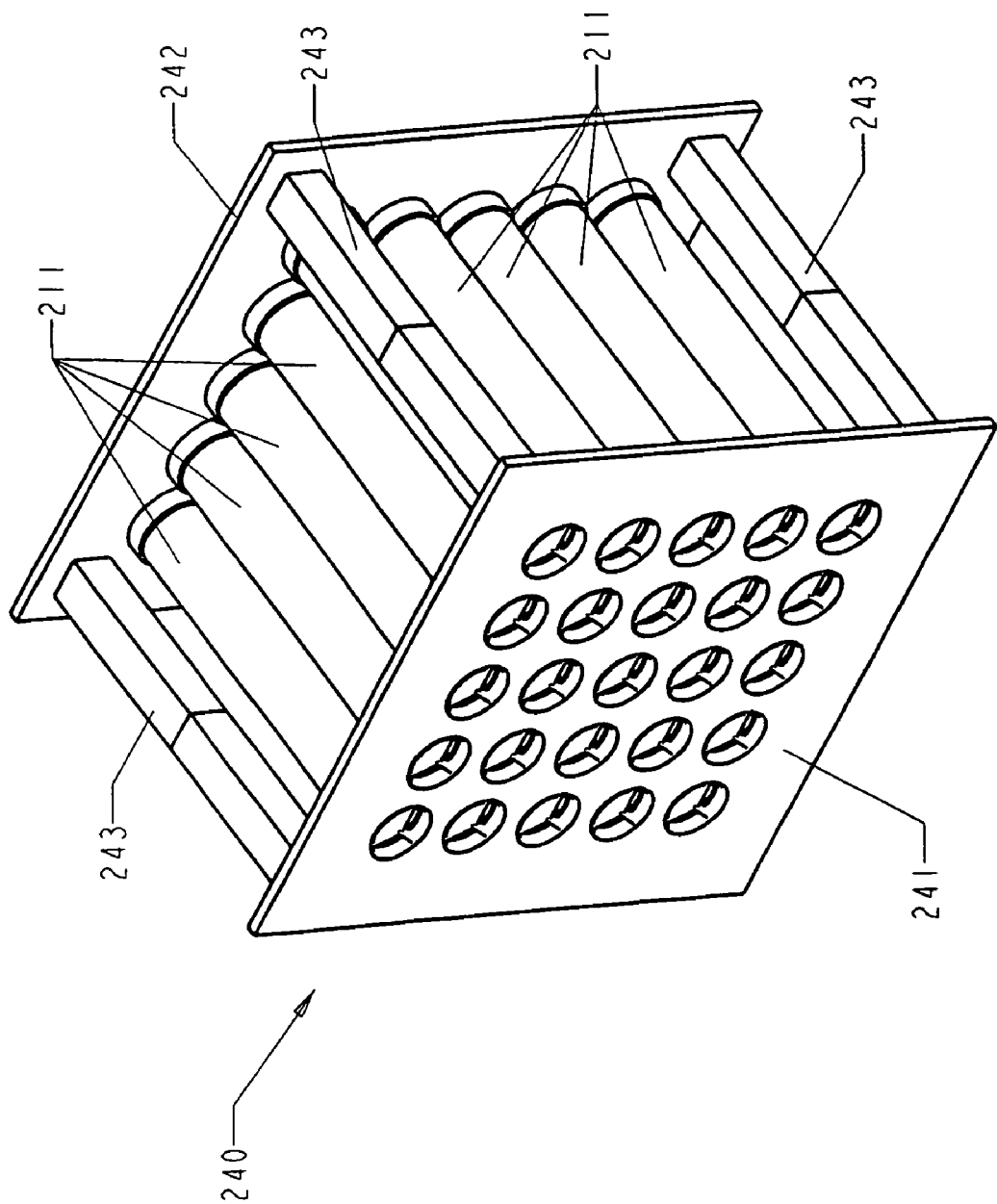

A plurality of these reactors can be mounted on a mounting member in a generally parallel configuration to achieve the desired level of residence time for effective destruction of contaminants. FIG. 9 shows a corresponding reactor assembly 240 for the embodiment of the reactor 211. The first mounting member 241 and the second mounting member 242 together hold the reactors 211 in place and form the reactor assembly 240.

The reactor 211 includes an air inlet 252 provided on one end of the reactor 211 and an air outlet 253 provided on another end of the reactor 211. The air inlet 252 and the air outlet 253 face to directions opposite with each other.

In use, air enters the reaction chamber 212 through the air inlet 252 and exits via the air outlet 253. By circulating air through the plasma-filled reaction chamber 212 inside the sub-assembly reactor, the pollutant particles and microbes in the air can be destructed.

Figure 10:
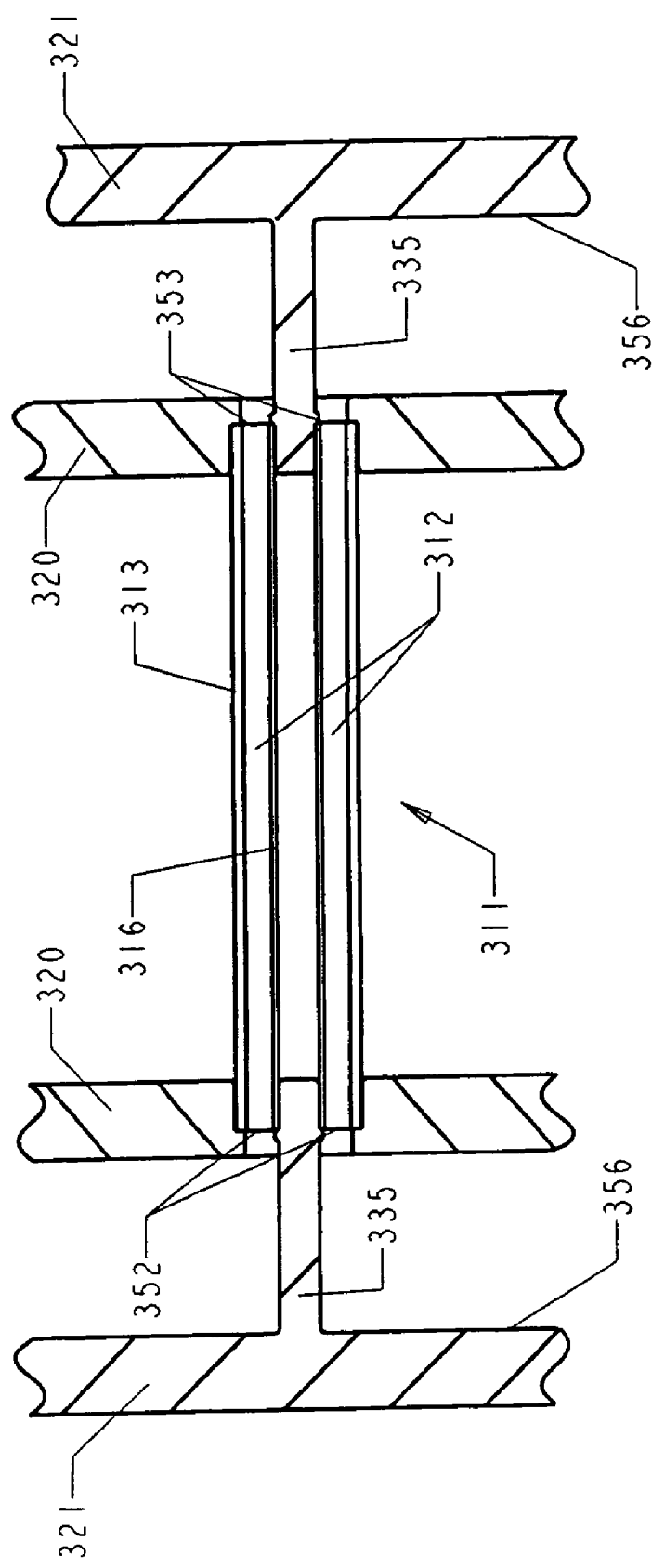
FIG. 10 is a cross-sectional side view of another embodiment of a reactor assembly showing a reactor and electrode mounting members.

FIG. 10 is a cross-sectional side view of another embodiment of a reactor assembly. In this embodiment, the reactor 311 is elongated and in cylindrical shape. The reactor 311 includes the outer electrode 313 and the inner electrode 316. The outer electrode 313 encompasses the inner electrode along the longitudinal axis of the reactor 311. The outer electrode 313 and the inner electrode 316 can be in a substantially concentric relationship. The outer electrode 313 and the inner electrode 316 define a reaction chamber 312 therebetween, which isolates the outer electrode 313 and the inner electrode 316. In the reaction chamber 312, electrical discharges are excited to generate plasma.

The inner electrode 316 includes an inner insulator and an inner electrode conductor. The outer electrode 313 includes an outer insulator and an outer electrode conductor. The inner and outer insulators are made of insulating materials, such as glass, and can be tubular in shape. The electrode conductors may be made of conducting sheets, mesh or deposits.

In this embodiment, the reactor 311 is fixed in a reactor assembly by electrode mounting members 320, 321. The reactor 311 includes an elongated outer electrode 313 and an elongated inner electrode 316 which define a reaction chamber 312. The outer electrode 313 may be held in place by the outer electrode mounting members 320, and each inner electrode 316 may be held in place by the inner electrode mounting members 321. Each of the inner electrode mounting members 321 includes a protruded portion 335 adapted to hold the inner electrode 316 in place. The protruded portion 335 is positioned generally perpendicular to the main surface 356 of the inner electrode mounting members 321 and along the longitudinal axis of the reactor 311. The reactor 311 includes an air inlet 352 and an air outlet 353. The air inlet 352 and the air outlet 353 face to directions opposite with each other.

A plurality of these reactors 311 can be held on mounting members 320 and 321 in a generally parallel configuration to achieve the desired level of residence time for effective destruction of contaminants. By circulating air through the plasma-filled reaction chamber 312 inside the integral insulator, the pollutant particles and microbes in the air can be destructed.

FIGS. 11a and 11b show another embodiment of a reactor assembly. In this embodiment, the reactor 411 is elongated and in cylindrical shape. The reactor 411 includes the outer electrode 413 and the inner electrode 416. The outer electrode 413 encompasses the inner electrode along a longitudinal axis of the reactor 411. The outer electrode 413 and the inner electrode 416 can be in a substantially concentric relationship. The outer electrode 413 and the inner electrode 416 define a reaction chamber 312 therebetween. In the reaction chamber 412, electrical discharges are excited to generate plasma.

The inner electrode 416 includes an inner insulator and an inner electrode conductor. The outer electrode 413 includes an outer insulator and an outer electrode conductor. The inner and outer insulators are made of insulating materials, such as glass, and can be tubular in shape. The electrode conductors may be made of conducting sheets, mesh or deposits.

In this embodiment, the reactor 411 is fixed in a reactor assembly by electrode mounting members 429. The insulator layer of the inner electrode 416 and the insulator layer of the outer electrode 418 are integrally built along the longitudinal axis of the reactor 411. As a result, a piece of mounting member 429 can hold both the inner electrode 416 and the outer electrode 418 at an end of the reactor 411. As shown in FIG. 11b, the cross-sectional front view of the reaction chamber 412 is in letter "C" shape. The reactor 411 includes an air inlet 452 and an air outlet 453. The air inlet 452 and the air outlet 453 face to directions opposite with each other.

A plurality of these reactors 411 can be held on mounting members 429 in a generally parallel configuration to achieve the desired level of residence time for effective destruction of contaminants. By circulating air through the plasma-filled reaction chamber 412 inside the integral insulator, the pollutant particles and microbes in the air can be destructed.

The reactor assembly or reactor can be incorporated into a conventional air ventilation system. For example, the reactor assembly or reactor can replace or work in conjunction with the filter units commonly used in air ventilation systems. The reactor assembly or reactor can be fitted to air circulation or air conditioning systems, such as air conditioners, air humidifiers, air de-humidifiers, and central air conditioning systems. Similarly, the reactor assembly or reactor can be fitted to air ventilation units, such as the air ventilator used in offices, to improve both the air entering a room and the air returning from the room to the main air circulating system. Accordingly, contaminated air can be disinfected before it enters the room, and contaminated air can be disinfected before it enters the main air ventilation circuit to avoid spreading the contaminants to other areas covered by the same air ventilation circuit.

It can be seen from the examples above that the plasma device(s) can be fitted to any air ventilation system to destroy microorganisms in the air to achieve the desired purification and disinfection.

It is to be understood that the phraseology and terminology employed herein are for the purpose of description and should not be regarded as limiting. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

What is claimed is:

1. An apparatus for air purification and disinfection using plasma, comprising:
   (a) a reactor assembly comprising a plurality of elongated reactors for generating plasma, each said reactor being held in parallel to each other in terms of electrical current and air flow and comprising an elongated inner electrode and an elongated outer electrode, the outer electrode encompassing at least a portion of the inner electrode along a longitudinal axis of the reactor, the outer and inner electrodes positioned in a substantially concentric relationship and defining a reaction chamber therebetween;
   (b) a single inner electrode mounting member holding together all inner electrodes of said reactor assembly at an end;
   (c) a single outer electrode mounting member holding together all outer electrodes of said reactor assembly at an end; and
   (d) a single power supply adapted to controlling and supplying electrical power to all inner and outer electrodes within said reactor assembly to generate plasma within the reaction chamber to purify and disinfect air flowing therethrough.

2. The apparatus of claim 1 wherein:
   the outer electrode comprises an insulator layer and an electrode conductor covered at the outer surface of the insulator layer; and
   the inner electrode comprises an insulator layer and an electrode conductor covered at the inner surface of the insulator layer.

3. The apparatus of claim 1 wherein:
   the outer electrode comprises an insulator layer and an electrode conductor embedded in the insulator layer; and
   the inner electrode comprises an insulator layer and an electrode conductor embedded in the insulator layer.

4. The apparatus of claim 1 wherein the reaction chamber of the reactor comprises an air inlet and an air outlet positioned at opposite ends thereof.

5. The apparatus of claim 4 wherein the outer electrode mounting member comprises an opening corresponding to the air inlet other air outlet of the reaction chamber of the reactor.

6. The apparatus of claim 1 wherein the inner electrode is longer than the outer electrode.

7. The apparatus of claim 1 wherein the inner electrode mounting member comprises a protruded portion holding the inner electrode.

8. The apparatus of claim 1, further comprising a set of filters, a coarse filter and blower, wherein said blower moves air going through said coarse filter, then said reaction chamber and finally said set of filters.

9. The apparatus of claim 1 wherein:
   the power supply comprises a control unit adapted to control the electrical power supplied to the inner and outer electrodes of the reactor; and
   disinfection effort of the apparatus is controlled by adjusting voltage and the ratio of on-cycles to off-cycles of the electrical power.

10. The apparatus of claim 9 wherein the waveform period of the electrical power and the on/off cycle of the electrical power are set to be shorter than the time that the air stays inside the reaction chamber.

* * * * *